(12) United States Patent
Shirasaki (10) Patent No.: US 6,736,252 B2
(45) Date of Patent: May 18, 2004

(54) WORK HOLDER FOR THROUGH HOLE EXAMINATION APPARATUS

(75) Inventor: Toru Shirasaki, Sakata (JP)

(73) Assignee: Seiko Epson Corporation (JP)

( * ) Notice: Subject to any disclaimer, the term of this patent is extended or adjusted under 35 U.S.C. 154(b) by 205 days.

(21) Appl. No.: 10/040,265

(22) Filed: Oct. 24, 2001

(65) Prior Publication Data
US 2002/0127092 A1 Sep. 12, 2002

(30) Foreign Application Priority Data

Oct. 27, 2000 (JP) ........................................ 2000-329362

(51) Int. Cl.[7] ................................................ B65G 15/64
(52) U.S. Cl. ........................ 198/345.3; 198/465.1; 198/867.01; 269/95; 100/229 R
(58) Field of Search ............................ 198/345.3, 465.1, 198/465.2, 465.3, 867.01–867.15, 803; 16/18 R, 19, 21, 24, 25; 100/229 R; 269/95

(56) References Cited

U.S. PATENT DOCUMENTS

| | | | | | |
|---|---|---|---|---|---|
| 2,034,509 A | * | 3/1936 | Haven | ............................ | 16/26 |
| 2,110,269 A | * | 3/1938 | Horvath | ........................ | 16/24 |
| 3,306,185 A | * | 2/1967 | Soman | .................... | 100/229 R |
| 3,456,481 A | * | 7/1969 | Zeitlin | ..................... | 100/229 R |
| 4,402,108 A | * | 9/1983 | Pannwitz | ........................ | 16/26 |
| 4,528,903 A | * | 7/1985 | Lerch | ..................... | 100/229 R |
| 5,234,205 A | * | 8/1993 | Shanley | ........................ | 269/99 |

FOREIGN PATENT DOCUMENTS

| | | |
|---|---|---|
| JP | 61-132843 | 6/1986 |
| JP | 07-111351 | 4/1995 |
| JP | 07-119744 | 5/1995 |

OTHER PUBLICATIONS

Communication from Japanese Patent Office re Counterpart Application No. 2000–329362.

* cited by examiner

*Primary Examiner*—Richard Ridley
(74) *Attorney, Agent, or Firm*—Harness, Dickey & Pierce, P.L.C.

(57) ABSTRACT

A work holder is provided for a through hole examination apparatus that reduces the generation of scrubbed-off metal powder caused by abrasion during the movements, and has a high operability. Also, it is an object to provide a work holder for a through hole examination apparatus that can readily adjust the holder to be parallel at low costs. A work holder 18 is provided for a through hole examination apparatus, which retains a workpiece having through holes provided therein and transfers the same between a work replacement operation region and a through hole examination region. A roller movement device 50 is mounted on the holder main body to enable a rolling movement thereof, and the roller movement device is made to be height-adjustable such that the parallel degree of the holder is adjustable.

14 Claims, 6 Drawing Sheets

WORK HOLDER FOR THROUGH HOLE EXAMINATION APPARATUS

TECHNICAL FIELD OF THE INVENTION

The present invention relates to a work holder for a through hole examination apparatus, and more particularly to a work holder that is suitable to an apparatus for examining the presence or absence of foreign matters in a through hole having a minute diameter.

BACKGROUND OF THE INVENTION

Figure 6:
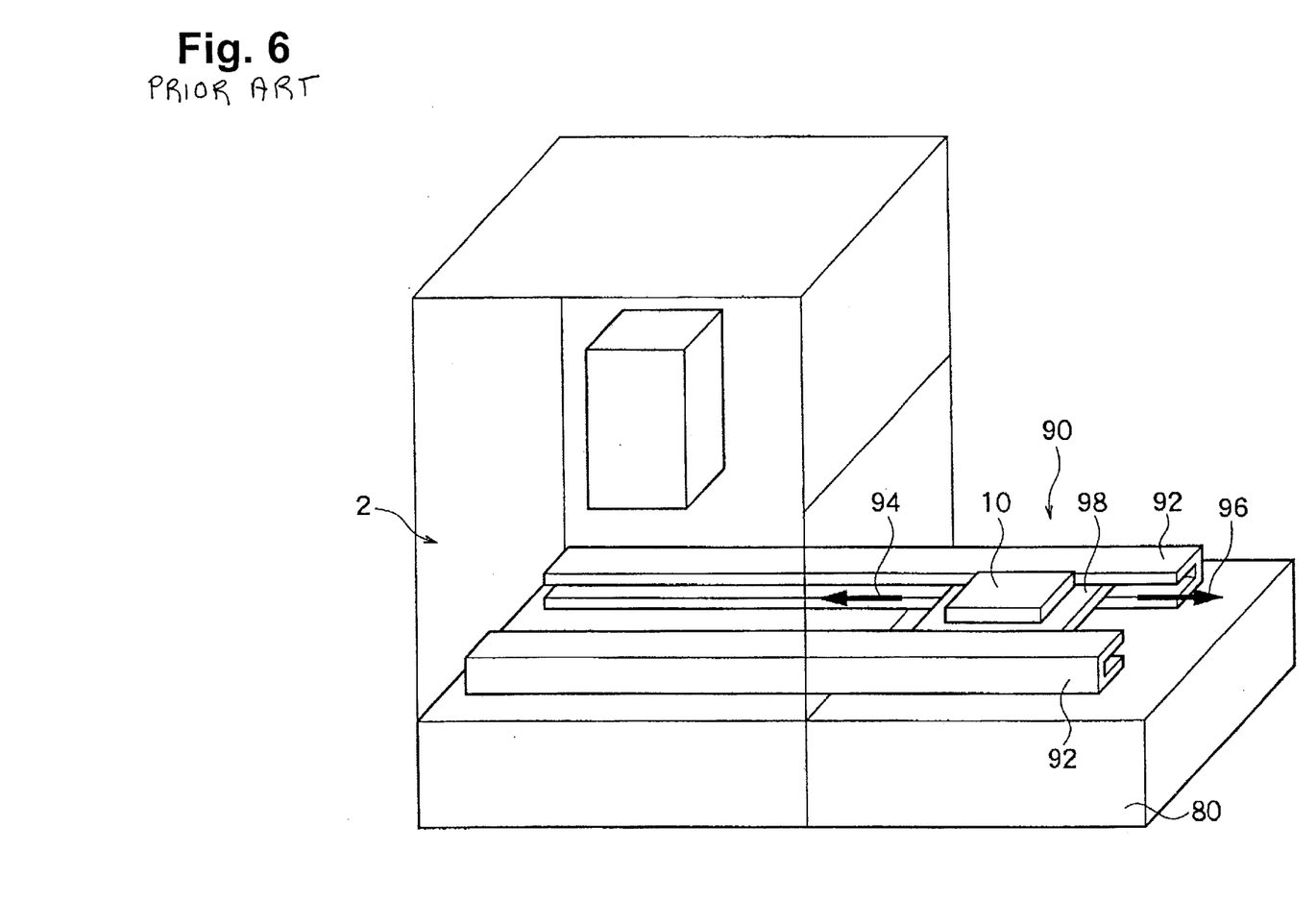
FIG. 6 shows an illustration to describe a linear guide in the conventional art.

Conventionally, in an apparatus for examining foreign matters in a through hole, a work holder that retains a work is moved by a linear guide 90 shown in FIG. 6 between a work replacement operation region 80 and a through hole examination region 2. In FIG. 6, two guides 92, each having a channel-shaped cross section with their opening sections facing each other, are disposed in a manner to extend from the work replacement operation region 80 and the through hole examination region 2. The work holder 98 that retains the workpiece 10 is supported at both ends by the respective guides, and disposed in a manner movable along the guides 92. The workpiece 10 is mounted on the work holder 98 in the work replacement operation region 80, moved along the guides 92 in a direction indicated by an arrow 94, and supplied to the through hole examination region 2. After the examination is completed, it is moved along the guides 92 in a direction indicated by an arrow 96, and the workpiece 10 is removed from the work holder 98 in the work replacement operation region 80.

Also, in an apparatus for examining foreign matters in minute through holes, light that passes through the through holes having minute diameters is examined. Accordingly, the holder is required to be parallel, and this requirement is dealt with by precisely processing the work holder 98 and the guides 98.

In the conventional technique that uses the linear guides described above, the work holder and the guides are brought in surface contact with one another, and scrubbed-off metal powder may be generated due to abrasion that occurs as the work holder moves along the guides, and may possibly be adhered inside the through holes to be examined. In order to improve the accuracy in positioning the work holder, margins in the measurements of the work holder and the guides need to be made smaller. However, this increases dust generation and makes the moving operation harder, which causes a problem of imposing excessive physical burden to the operators.

Further, while the holder is required to be parallel in the apparatus for examining foreign matters in minute through holes, when the work holder is made larger so that multiple workpieces can be mounted at once, the countermeasure of precisely processing the work holder is technically and economically difficult. Furthermore, once the parallel state is destroyed by abrasion or the like in the conventional system, the correction thereof is extremely difficult.

It is an object of the present invention to provide a work holder for a through hole examination apparatus that reduces generation of scrubbed-off metal powder caused by abrasion during the movements, and has a high operability. Also, it is an object to provide a work holder for a through hole examination apparatus that can readily adjust the parallel degree of the holder at low costs. Moreover, it is an object to provide a work holder for a through hole examination apparatus that can realize an easy and correct examination of foreign matters in through holes at low costs.

SUMMARY OF THE INVENTION

To achieve the objects described above, a work holder for a through hole examination apparatus in accordance with the present invention pertains to a work holder for a through hole examination apparatus that retains a workpiece having through holes provided therein and transfers the same between a work replacement operation region and a through hole examination region, wherein a roller movement device is mounted on a main body of the holder to enable a rolling movement thereof, and the roller movement device is made to be height-adjustable such that the parallel degree of the holder is adjustable.

The above provides a structure in which the roller movement device is mounted on the holder's main body to enable a rolling movement thereof, and therefore provides a work holder for a through hole examination apparatus, which generates less scrubbed-off metal powder, and has a good operability in which the holder can be readily moved. Also, the above provides a structure in which the roller movement device is made to be height-adjustable such that the parallel degree of the holder can be adjusted, and therefore provides a work holder for a through hole examination apparatus, which can readily adjust the parallel degree of the holder at low costs.

Also, the roller movement device may preferably be formed from a ball bearing that is equipped with a ball that can roll on a running surface in a point-contact state.

Furthermore, the roller movement device may preferably be provided with a roller movement support member that engages by screw threads with and passes through the holder main body, and a penetrated leading end thereof may preferably be provided with a slit for mounting a rotation tool.

In addition, the work holder for a through hole examination apparatus may preferably be formed from a lower jig on which a workpiece is mounted, and an upper jig that presses the workpiece between itself and the lower jig, wherein the lower jig may preferably have a positioning notch for positioning itself with respect to the through hole examination region and at least one pair of pins provided for positioning the upper jig, and the upper jig may preferably be equipped with notches for engaging the positioning pins.

More particularly, a work holder for a through hole examination apparatus, which retains a workpiece having through holes perforated therein and transfers the same between a work replacement operation region and a through hole examination region, is equipped with: a holder main body that is formed from a lower jig on which a workpiece is mounted and an upper jig that presses the workpiece between itself and the lower jig, wherein the lower jig has a positioning notch for positioning itself with respect to the through hole examination region and at least one pair of pins provided for positioning the upper jig, and the upper jig is equipped with notches for engaging the positioning pins; and a roller movement device that is formed from a ball bearing equipped with a ball that can roll on a running surface in a point-contact state is mounted on the main body of the holder at a peripheral section thereof, wherein the roller movement device is provided with a roller movement support member that engages by screw threads with and passes through the holder main body, and a penetrated leading end thereof is provided with a slit for mounting a rotation tool, such that the height can be adjusted.

DETAILED DESCRIPTION OF THE PREFERRED EMBODIMENTS OF THE PRESENT INVENTION

An embodiment of the present invention is described in detail below with reference to the accompanying drawings. In the embodiment, a work holder for a through hole examination apparatus in accordance with the present invention is applied to a work holder that transfers workpieces to an apparatus for examining foreign matters in through holes in which light passing through a plurality of through holes having the same size in a workpiece is taken in at once as image data by a relative plane movement of a line sensor camera, and spot areas corresponding to the plurality of through holes that are taken in are compared with one another to judge the presence or absence of foreign matters.

Figure 2:
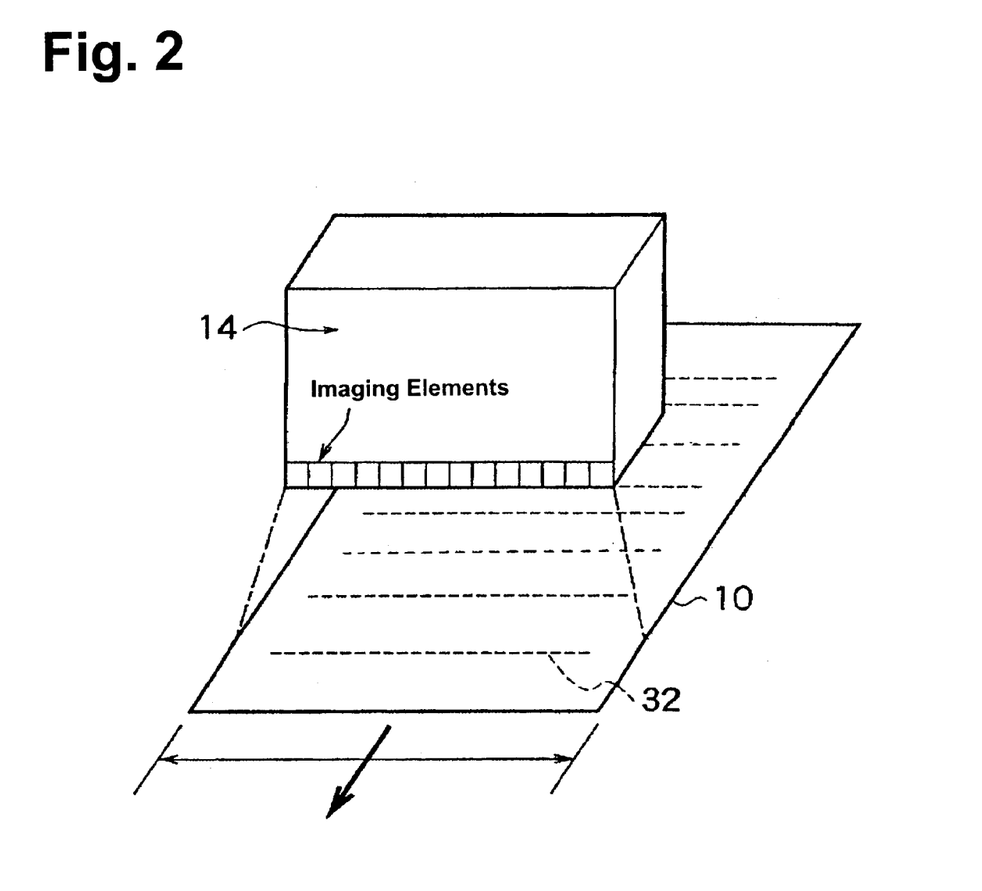
FIG. 2 is an illustration to describe work.

FIG. 2 shows an example of a workpiece. The workpiece 10 has a plurality of through holes 32, in other words, pierced holes, having the same size. In the case of through holes having minute diameters, if a minute foreign matter adheres in a through hole, the through hole is blocked, and the original function of the through hole cannot be attained. Accordingly, it is necessary to examine whether a foreign matter is not adhered in the through hole in the workpiece, and at the same time it is also necessary to prevent adhesion of minute foreign matters to through holes in the examination apparatus.

Figure 3:
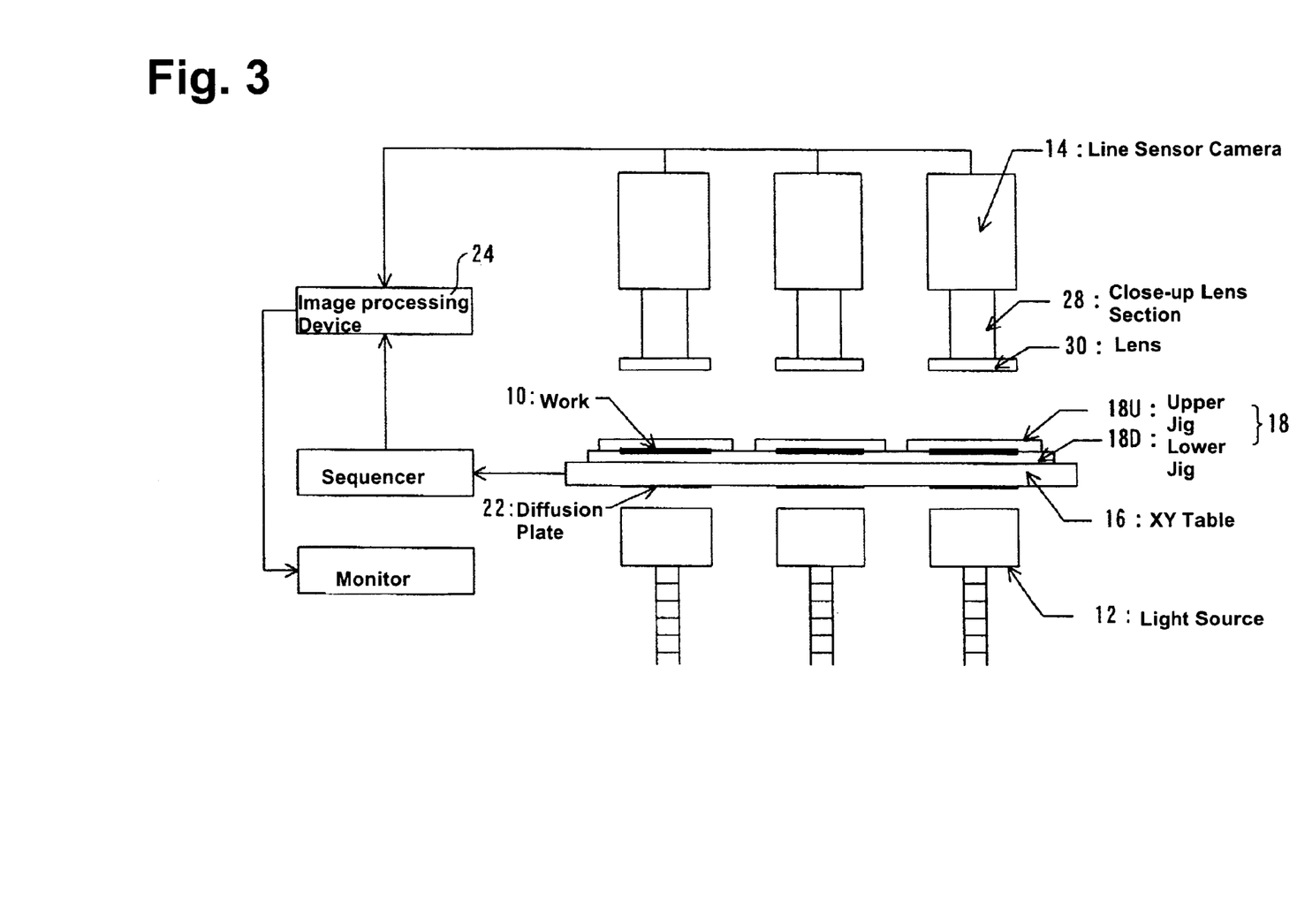
FIG. 3 shows a block diagram of an apparatus for examining foreign matters in through holes.

FIG. 3 shows a structure of an apparatus for examining foreign matters in through holes. The examination apparatus has a structure in which a light source 12 is disposed on the side of a lower surface of a plate-shaped workpiece 10 having a plurality of through holes arranged in columns to irradiate light from behind toward the through holes. On the other hand, a line sensor camera 14 having a plurality of pixels arranged in a column is disposed on the side of an upper surface of the workpiece 10 wherein the light passing through the through holes is photographed by the camera 14. The image data is input in an image processing device 24 whereby a detection of foreign matters is conducted by using the characteristic in which, when a foreign matter is present in a through hole, an area value of the through hole becomes smaller as a result of the foreign matter blocking the light. Since the apparatus examines light passing through a through hole having a minute diameter, the area of the passing light may substantially vary depending on the inclination of the workpiece 10. Therefore, the workpiece 10 and the work holder 18 are required to be parallel with one another. It is noted that, since the example shown in the figure examines three workpieces 10 at once, the light source 12 and the sensor camera 14 are provided in three pairs. However, the number of workpieces to be examined at once can be any number, and light sources and sensor cameras in the corresponding number can be provided in the apparatus.

In the examination of through holes which uses the apparatus described above, the workpiece 10 needs to be transferred to a predetermined position on an XY table 16 that defines an examination region, and upon completion of the examination, the workpiece 10 needs to be moved from the examination region to the work replacement operation region where it is replaced with a new workpiece. In order to transfer the workpiece, a work holder 18 on which the workpiece 10 is mounted is used.

Figure 1:
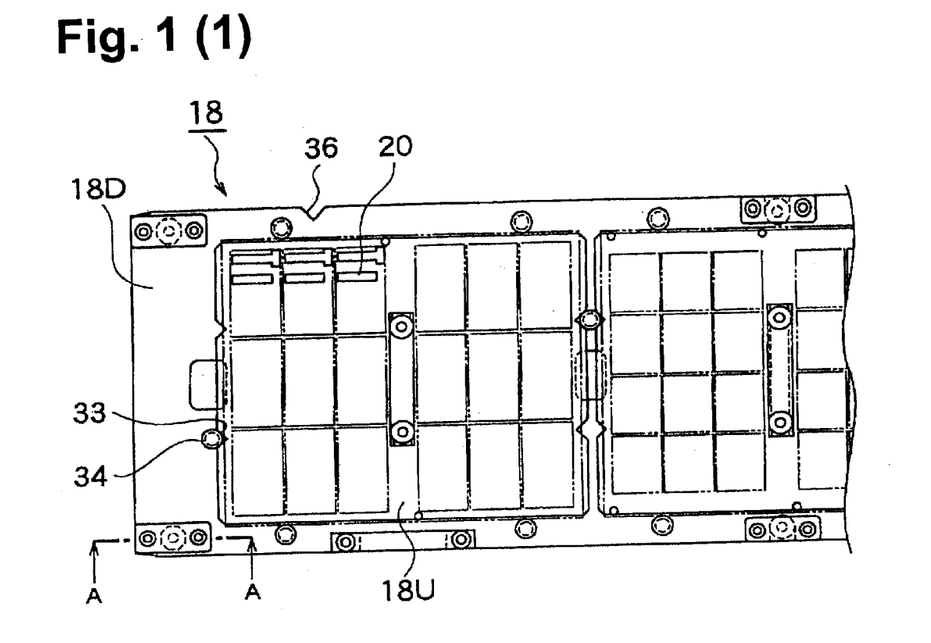
FIG. 1 shows a plan view and a front view of a work holder for a through hole examination apparatus in accordance with the present invention.

FIG. 1 (1) shows a plan view of the work holder 18 and FIG. 1 (2) shows a front view of the work holder.

The work holder 18 is formed from a holder main body composed of a lower jig 18D and an upper jig 18U, and a roller movement device 50 that is mounted on the holder main body for roller movements thereof The lower jig 18D that composes the holder main body is provided with a recessed section formed on its upper surface section for mounting the workpiece 10 thereon. The recessed section has measurements that match the outer configuration of the workpiece 10. In the present embodiment, three recessed sections are formed such that three workpieces 10 are mounted thereon at a time. On the other hand, the upper jig 18U is formed in a manner to be coupled to and mounted on the recessed section to push the workpiece 10 mounted in the recessed section from above to thereby fixedly retain the workpiece. Three upper jigs 18U are used corresponding to the three recessed sections for one lower jig.

The work holder 18 is transferred to the XY table 16 in the through hole examination region and needs to be retained at a predetermined position. For this reason, a V-shaped notch 36 is provided on a side edge of the lower jig 18D for positioning with respect to the XY table 16. Also, for examination of through holes of a workpiece, the examination apparatus irradiates light from the lower surface side of the XY table 16, and detects light passing through the through holes of the workpiece by a line sensor disposed in a position above. For this reason, the recessed section of the lower jig 18D is provided with a hole that allows light to be irradiated onto the lower surface of the workpiece 10.

In the mean time, the upper jig 18U, which is mounted in the recessed section in a manner described above, is provided with V-shaped notches 33 on opposing side edges such that it is retained at an appropriate position. In the mean time, one pair of standing pins 34 to be engaged with the notches 33 are provide on an edge section of each of the recessed sections of the lower jig 18D. Accordingly, by engaging the V-shaped notches 33 with the pins 34 and mounting the upper jig 18U in the recessed section of the lower jig 18D, they are readily positioned with respect to one another. The notches at each of the recessed sections 33 and the pins 34 are provided in engaging positions that are symmetrical about a point but slightly shifted from diagonal lines of the recessed section. The upper jig 18U is provided with slits 20 formed therein corresponding to the columns of through holes provided in the workpiece 10. The passing light passes through the slits 20 and is photographed by the line sensor camera 14.

Figure 4:
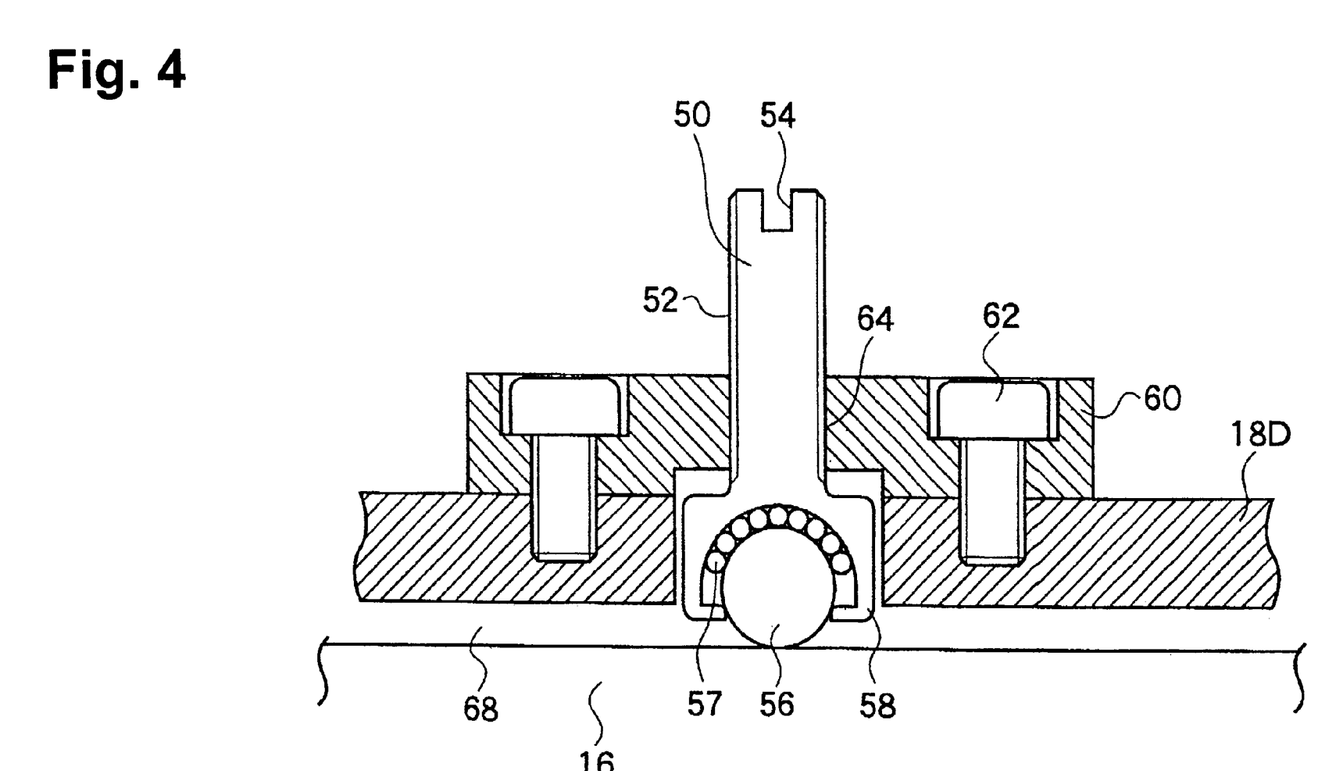
FIG. 4 shows a cross-sectional view taken along a line A—A of FIG. 1.

Roller movement devices 50 for roller movement of the work holder 18 are provided at four corners and central sections in the longitudinal direction of the lower jig 18D. In the illustrated example, the total of six roller movement devices 50 are provided. However, they can be provided in any other number in view of the amount of bend of the lower jig and the convenience in the parallel adjustment. A structure of the roller movement device is shown in FIG. 4. This figure is a cross-sectional view taken along a line A—A of FIG. 1, and shows in detail a portion where the roller movement device is mounted. A roller movement device mounting plate 60 is disposed on the upper surface side of the lower jig 18D and fixed to the lower jig 18D by bolts 62. A female screw 64 is provided in a central portion of the roller movement device mounting plate 60.

The roller movement device 50 includes a roller movement supporting member that connects a main ball 56 which is its roller movement section and the roller movement device mounting plate 60. The roller movement supporting member is provided with one male screw 52 for mounting, which is coupled by screw threads with the female screw 64, whereby the roller movement device 50 is mounted on the holder main body, and at the same time the holder main body is supported by the roller movement device 50. To provide the holder main body with a height adjustable feature, the roller movement supporting member is mounted in a manner to pass through the roller movement device mounting plate 60, and has a groove shaped slit 54 having parallel surfaces at its upper end portion for mounting a rotation tool.

In the mean time, the main ball 56 is provided at a lower end of the roller movement device 50 to maintain the holder main body in a point contact state with respect to the YX table 16. As a result, the holder main body is disposed separated in a vertical direction by a gap 68 from the XY table 16. Small balls 57 are provided between a casing 58 and the main ball 56 such that the main ball 56 can freely rotate as a ball bearing, and the work holder 18 can be moved on rollers. It is noted that a wheel or the like other than the ball described above may be used as a roller movement section of the roller movement device.

Figure 5:
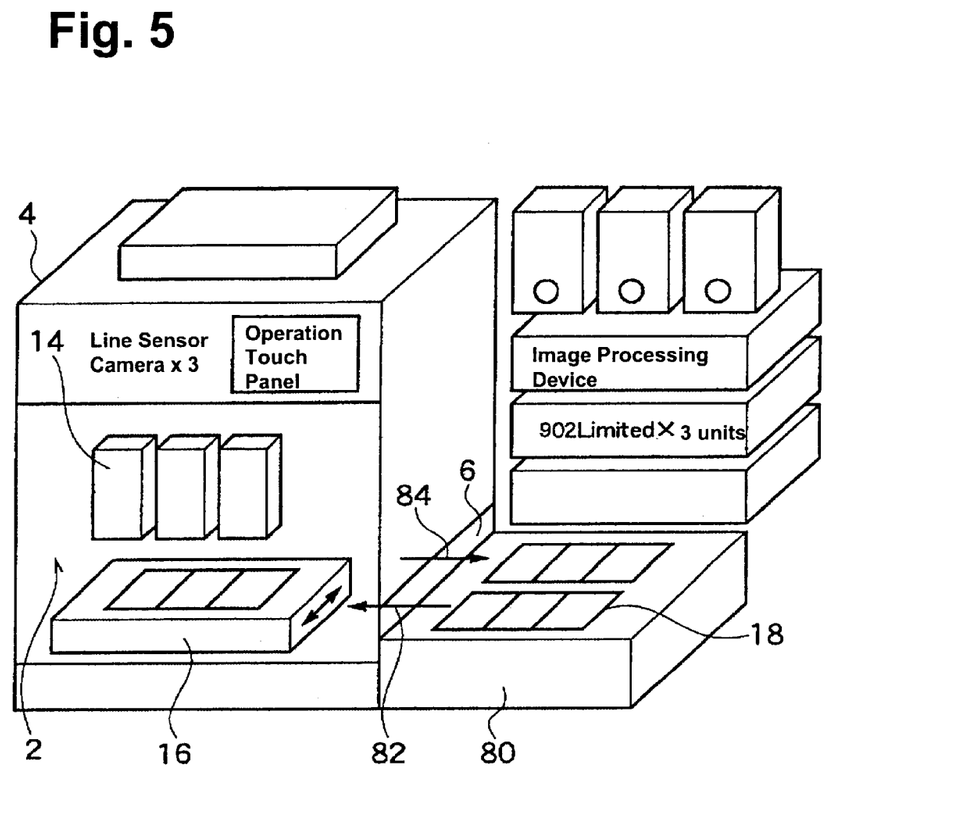
FIG. 5 is an illustration to describe the relation between an apparatus for examining foreign matters in through holes and a work replacement operation region.

Next, operations of feeding and discharging the workpiece 10 in accordance with the present embodiment are described. FIG. 5 shows the relation between the apparatus for examining foreign matters in through holes 2 and the work replacement operation region 80. The examination apparatus 2 and the work replacement operation region 80 are disposed in an environment where foreign matters are thoroughly removed, such as a clean room. In addition, the apparatus for examining foreign matters in through holes 2 is covered by a case 4 in order to prevent very fine foreign matters from adhering to the workpiece. Accordingly, setting of the workpiece on the holder main body is conducted in the work replacement operation region 80 provided adjacent to the examination apparatus 2. First, the lower jig 18D is placed in the work replacement operation region 80, a workpiece is set in the recessed section provided therein, and then the upper jig 18U is set over it. The upper jig 18U is positioned with respect to the lower jig 18D by the pair of notches provided in the upper jig abutting the pair of standing pins 34 provided on the lower jig 18D (see FIG. 1). In the present embodiment, three workpieces are similarly set on the holder main body. After the workpieces are set, the work holder 18 is passed through a gap 6 formed in the case 4, and fed onto the XY table 16 of the examination apparatus 2 as indicated by an arrow 82. The holder 18 is positioned with respect to the XY table 16 by its notch 36 abutting the standing pin (not shown in the figure) provided oh the XY table 16 (see FIG. 1). The workpieces are positioned in this manner such that through holes are located at the same positions even when the workpieces are replaced, which realizes an accurate examination of foreign matters in through holes. When the examination is completed, the workpieces and the work holder 18 are moved through the gap 6 and discharged into the work replacement operation region 80 as indicated by an arrow 84, and the workpieces are removed from the holder main body on the work replacement operation region.

During the feeding and discharging operations, the main ball 56 that composes the roller movement device 50 is always in a point contact with the work replacement operation region 80 and the XY table 16. Even when the work holder 18 does not linearly move but moves in a zigzag manner, the main ball 56 follows the movements and freely rolls. As a result, abrasions hardly ever occur between the ball and the work replacement operation region 80 or the XY table 16 and scrubbed-off metal power is hardly ever generated. Accordingly, adhesion of very fine foreign matters such as scrubbed-off metal power to the through holes of the workpieces is reduced. Also, even when the operator manually feeds or discharges the holder 18, it can be readily moved. This provides an excellent operability. Furthermore, the V-shaped notch 36 of the lower jig 18 is abutted to the pin on the XY table, and the V-shaped notches 33 of the upper jig 18U are aligned with the pins 34 of the lower jig to thereby mount the upper jig on the recessed section of the lower jig, such that the workpieces 10 can be accurately positioned, and an accurate examination of foreign matters in through holes can be realized.

Next, a parallel adjustment operation for workpieces 10 in accordance with the present embodiment is described. Workpieces and the work holder 18 are placed on the XY table at predetermined intervals, such as, for example, everyday before the examinations start, to check by a parallel checking apparatus if the workpieces are parallel. When the parallel state is not present, a tool may be mounted on the slit 54 to rotate the roller movement support member of the roller movement device 50 shown in FIG. 4, which is located in an area that is considered to be the cause. As a result, the corresponding portion of the holder main body is moved in a vertical direction with respect to the XY table, whereby the holder main body can be adjusted to be parallel. The operation described above may be repeated several times to achieve the parallel disposition of the workpieces. It is noted that since the parallel disposition of the workpieces is achieved by the holder main body. Therefore, once the parallel disposition is confirmed, it is not necessary to check if workpieces are parallel every time workpieces are replaced.

In this manner, when the parallel state is not present, for any one of the roller movement devices that supports a portion that is considered to be the cause or a peripheral portion thereof, the screw mounted on the roller movement support member thereof is adjusted such that the parallel state of the entire body of the holder can be adjusted. Accordingly, workpieces can be readily adjusted to be parallel. Also, since it is not necessary to provide an independent height adjusting device other than the roller movement device, and it is not necessary to precisely process the holder itself, the holder can be readily adjusted to be parallel. In other words, the work holder 18 is a large size holder onto which three workpieces are fixed, and it may be difficult to precisely process the holder itself. However, in accordance with the present embodiment, it is not necessary to precisely process the holder itself, and the holder can be readily adjusted to be parallel.

In the embodiment described above, in particular, the roller movement device is composed of a ball bearing equipped with a ball that can roll on a running surface in a point contact state. As a result, abrasions do not occur between the ball and the working surface, such that the generation of scrubbed-off metal powder can be reduced. Furthermore, the roller movement device is provided with a structure in which a roller movement support member engages by screw threads with and passes through the holder main body, and a penetrated leading end thereof is provided with a slit for mounting a rotation tool. As a result, by adjusting only one screw mounted on the roller movement device, the parallel state of the holder can be substantially readily adjusted. In addition, the work holder for a through hole examination apparatus is provided with a structure equipped with a lower jig on which a workpiece is mounted, and an upper jig that presses the workpiece between itself and the lower jig, wherein the lower jig has a positioning notch for positioning itself with respect to the through hole examination region and at least one pair of pins provided for positioning the upper jig, and the upper jig is equipped with notches for engaging the positioning pins. As a result, an easy, low cost and accurate examination of foreign matters in through holes can be realized.

What is claimed is:

1. A workpiece holder for a through hole examination apparatus that retains a workpiece having through holes provided therein and transfers the workpiece between a workpiece replacement operation region and a through hole examination region, the workpiece holder comprising:

a main body having an upper jig and a lower jig which are operable to hold a workpiece therebetween; and a roller movement device directly mounted on said lower jig to enable a rolling movement of said main body, said roller movement device being height-adjustable.

2. The workpiece holder according to claim 1, wherein the roller movement device further comprises a ball bearing including a ball that can roll on a running surface.

3. The workpiece holder according to claim 1, wherein the roller movement device further comprises a roller movement device support member threadingly engaging said main body, said roller movement device support member being rotatable relative to said main body to height-adjust the workpiece holder relative to a running surface.

4. The workpiece holder according to claim 3 wherein said exposed portion of said roller movement device support member includes a slit for receiving rotation.

5. The workpiece holder according to claim 1, wherein said lower jig includes a positioning notch for positioning said lower jig with respect to the through hole examination region and at least one pair of pins for positioning said upper jig relative to said lower jig, said upper jig having notches for engaging said positioning pins.

6. A workpiece holder for a through hole examination apparatus, which retains a workpiece having through holes perforated therein and transfers the workpiece between a workpiece replacement operation region and a through hole examination region, the workpiece holder comprising:

a holder main body including a lower jig on which said workpiece is mounted and an upper jig that presses the workpiece between the upper jig and the lower jig, said lower jig having a positioning notch for positioning said lower jig with respect to said through hole examination region and at least one pair of pins for positioning the upper jig relative to the lower jig, said upper jig including notches for engaging the positioning pins; and a roller movement device mounted to a peripheral portion of said holder main body, said roller movement device including a ball bearing having a ball that can roll on a running surface, the roller movement device also including a roller movement support member threadingly engaging the holder main body, an exposed portion of said roller movement support member including a slit for receiving a rotation tool, such that a height of the holder main body can be adjusted.

7. A workpiece holder for a through hole examination apparatus comprising:

a main body having an upper jig and a lower jig, said upper and lower jigs defining an interstitial space operable to receive the workpiece;

a rolling member directly coupled to said lower jig; and a height adjustable mechanism operably coupled between said lower jig and said rolling member for height-adjusting said main body relative to a running surface.

8. The workpiece holder of claim 7 wherein said rolling member further comprises a ball bearing.

9. The workpiece holder of claim 7 wherein said height adjustable mechanism further comprises a support member adjustably engaging said main body at one end and rotatably coupled to said rolling member at a second end.

10. The workpiece holder of claim 7 wherein said support member threadingly engages said main body.

11. The workpiece holder of claim 10 wherein said support member includes an accessible portion having an engagement mechanism adapted to receive a rotation.

12. The workpiece holder of claim 11 wherein said engagement mechanism further comprises a slit.

13. The workpiece holder of claim 7 wherein said main body further comprises:

an upper jig positioning pin extending from said lower jig; and a positioning notch formed on said upper jig and adapted to receive said positioning pin therein to position said upper jig relative to said lower jig.

14. The workpiece holder of claim 13 wherein said lower jig includes a lower jig positioning pin extending therefrom, said lower jig positioning pin being adapted to position said lower jig relative to a workpiece replacement operation area.

* * * * *